(12) United States Patent
Ringold

(10) Patent No.: US 8,788,296 B1
(45) Date of Patent: Jul. 22, 2014

(54) SYSTEMS AND METHODS FOR PROVIDING NOTIFICATIONS OF AVAILABILITY OF GENERIC DRUGS OR PRODUCTS

(75) Inventor: James Morgan Ringold, Lawrenceville, GA (US)

(73) Assignee: McKesson Financial Holdings (BM)

( * ) Notice: Subject to any disclaimer, the term of this patent is extended or adjusted under 35 U.S.C. 154(b) by 246 days.

(21) Appl. No.: 12/696,717

(22) Filed: Jan. 29, 2010

(51) Int. Cl.
*G06Q 40/00* (2012.01)
*G06Q 40/08* (2012.01)
*G06Q 50/22* (2012.01)

(52) U.S. Cl.
CPC ............... *G06Q 40/08* (2013.01); *G06Q 50/22* (2013.01)
USPC .................................................. 705/4; 705/2

(58) Field of Classification Search
CPC .............................. G06Q 40/08; G06Q 50/22
USPC .......................................................... 705/2–4
See application file for complete search history.

(56) References Cited

U.S. PATENT DOCUMENTS

| | | | |
|---|---|---|---|
| 4,674,041 A | 6/1987 | Lemon et al. | |
| 4,723,212 A | 2/1988 | Mindrum et al. | |
| 4,910,672 A | 3/1990 | Off et al. | |
| 5,007,641 A | 4/1991 | Seidman | |
| 5,080,364 A | 1/1992 | Seidman | |
| 5,173,851 A | 12/1992 | Off et al. | |
| 5,201,010 A | 4/1993 | Deaton et al. | |
| 5,235,702 A | 8/1993 | Miller | |
| 5,237,620 A | 8/1993 | Deaton et al. | |
| 5,301,105 A | 4/1994 | Cummings | |
| 5,305,196 A | 4/1994 | Deaton et al. | |
| 5,327,508 A | 7/1994 | Deaton et al. | |
| 5,359,509 A | 10/1994 | Little et al. | |
| 5,388,165 A | 2/1995 | Deaton et al. | |
| 5,430,644 A | 7/1995 | Deaton et al. | |
| 5,448,471 A | 9/1995 | Deaton et al. | |
| 5,544,044 A | 8/1996 | Leatherman | |
| 5,550,734 A | 8/1996 | Tarter et al. | |
| 5,588,649 A | 12/1996 | Blumberg et al. | |

(Continued)

FOREIGN PATENT DOCUMENTS

| CA | 2482370 A1 | 3/2006 |
|---|---|---|
| EP | 1310895 A2 | 11/2002 |

(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Sheetal R Rangrej
(74) *Attorney, Agent, or Firm* — Sutherland Asbill & Brennan LLP

(57) ABSTRACT

Systems and methods may provide notifications of availability of generic drugs or products. The systems and methods may include receiving, from a healthcare provider computer, a healthcare claim transaction request that identifies a product for a patient; determining that the product identified by the healthcare claim transaction request is a non-generic product or a branded product; determining that a generic equivalent for the product identified by the healthcare claim transaction request will become available on a future date; generating a generic notification message indicating the availability of generic equivalent for the product on the future date; and delivering or directing a delivery of the generic notification message.

20 Claims, 5 Drawing Sheets

(56) References Cited

U.S. PATENT DOCUMENTS

| | | |
|---|---|---|
| 5,592,560 A | 1/1997 | Deaton et al. |
| 5,612,868 A | 3/1997 | Off et al. |
| 5,621,812 A | 4/1997 | Deaton et al. |
| 5,628,530 A | 5/1997 | Thornton |
| 5,638,457 A | 6/1997 | Deaton et al. |
| 5,642,485 A | 6/1997 | Deaton et al. |
| 5,644,723 A | 7/1997 | Deaton et al. |
| 5,644,778 A | 7/1997 | Burks et al. |
| 5,649,114 A | 7/1997 | Deaton et al. |
| 5,659,469 A | 8/1997 | Deaton et al. |
| 5,675,662 A | 10/1997 | Deaton et al. |
| 5,687,322 A | 11/1997 | Deaton et al. |
| 5,704,044 A | 12/1997 | Tarter et al. |
| 5,748,907 A | 5/1998 | Crane |
| 5,749,907 A | 5/1998 | Mann |
| 5,832,447 A | 11/1998 | Rieker et al. |
| 5,832,457 A | 11/1998 | O'Brien |
| 5,845,255 A | 12/1998 | Mayaud |
| 5,857,175 A | 1/1999 | Day et al. |
| 5,892,827 A | 4/1999 | Beach et al. |
| 5,892,900 A | 4/1999 | Ginter et al. |
| 5,915,007 A | 6/1999 | Klapka |
| 5,926,795 A | 7/1999 | Williams |
| 5,950,169 A | 9/1999 | Borghesi et al. |
| 5,956,736 A | 9/1999 | Hanson et al. |
| 5,963,915 A | 10/1999 | Kirsch |
| 5,970,469 A | 10/1999 | Scroggie et al. |
| 5,974,399 A | 10/1999 | Giuliani et al. |
| 5,991,750 A | 11/1999 | Watson |
| 6,000,828 A | 12/1999 | Leet |
| 6,006,242 A | 12/1999 | Poole et al. |
| 6,012,035 A | 1/2000 | Freeman, Jr. et al. |
| 6,014,634 A | 1/2000 | Scroggie et al. |
| 6,021,392 A | 2/2000 | Lester et al. |
| 6,026,370 A | 2/2000 | Jermyn |
| 6,041,309 A | 3/2000 | Laor |
| 6,055,573 A | 4/2000 | Gardenswartz et al. |
| 6,067,069 A | 5/2000 | Krause |
| 6,067,524 A | 5/2000 | Byerly et al. |
| 6,073,104 A | 6/2000 | Field |
| 6,185,541 B1 | 2/2001 | Scroggie et al. |
| 6,195,612 B1 | 2/2001 | Pack-Harris |
| 6,202,923 B1 | 3/2001 | Boyer |
| 6,205,455 B1 | 3/2001 | Umen |
| 6,208,973 B1 | 3/2001 | Boyer et al. |
| 6,224,387 B1 | 5/2001 | Jones |
| 6,240,394 B1 | 5/2001 | Uecker |
| 6,260,758 B1 | 7/2001 | Blumberg |
| 6,278,979 B1 | 8/2001 | Williams |
| 6,282,516 B1 | 8/2001 | Giuliani |
| 6,298,330 B1 | 10/2001 | Gardenswartz et al. |
| 6,304,849 B1 | 10/2001 | Uecker et al. |
| 6,307,940 B1 | 10/2001 | Yamamoto et al. |
| 6,307,958 B1 | 10/2001 | Deaton et al. |
| 6,321,210 B1 | 11/2001 | O'Brien et al. |
| 6,324,516 B1 | 11/2001 | Shults et al. |
| 6,330,546 B1 | 12/2001 | Gopinathan et al. |
| 6,334,108 B1 | 12/2001 | Deaton et al. |
| 6,341,265 B1 | 1/2002 | Provost et al. |
| 6,343,271 B1 | 1/2002 | Peterson et al. |
| 6,351,735 B1 | 2/2002 | Deaton et al. |
| 6,377,935 B1 | 4/2002 | Deaton et al. |
| 6,424,949 B1 | 7/2002 | Deaton et al. |
| 6,427,020 B1 | 7/2002 | Rhoads |
| 6,484,146 B2 | 11/2002 | Day et al. |
| 6,542,902 B2 | 4/2003 | Dulong et al. |
| 6,584,448 B1 | 6/2003 | Laor |
| 6,632,251 B1 | 10/2003 | Rutten et al. |
| 6,671,692 B1 | 12/2003 | Marpe et al. |
| 6,671,693 B1 | 12/2003 | Marpe et al. |
| 6,684,195 B1 | 1/2004 | Deaton et al. |
| 6,714,918 B2 | 3/2004 | Hillmer et al. |
| 6,757,898 B1 | 6/2004 | Ilsen et al. |
| 6,769,228 B1 | 8/2004 | Mahar |
| 6,795,809 B2 | 9/2004 | O'Brien et al. |
| 6,859,780 B1 | 2/2005 | Cunningham |
| 6,879,959 B1 | 4/2005 | Chapman et al. |
| 6,885,994 B1 | 4/2005 | Scroggie et al. |
| 7,013,284 B2 | 3/2006 | Guyan et al. |
| 7,024,374 B1 | 4/2006 | Day et al. |
| 7,058,584 B2 | 6/2006 | Kosinski et al. |
| 7,058,591 B2 | 6/2006 | Giuliani et al. |
| 7,111,173 B1 | 9/2006 | Scheidt |
| 7,155,397 B2 | 12/2006 | Alexander et al. |
| 7,225,052 B2 | 5/2007 | Foote et al. |
| 7,228,285 B2 | 6/2007 | Hull et al. |
| 7,233,913 B2 | 6/2007 | Scroggie et al. |
| 7,309,001 B2 | 12/2007 | Banfield et al. |
| 7,356,460 B1 | 4/2008 | Kennedy et al. |
| 7,380,707 B1 | 6/2008 | Fredman |
| 7,401,027 B2 | 7/2008 | Moore et al. |
| 7,415,426 B2 | 8/2008 | Williams et al. |
| 7,418,400 B1 | 8/2008 | Lorenz |
| 7,426,480 B2 | 9/2008 | Granger et al. |
| 7,597,247 B2 | 10/2009 | Helmin et al. |
| 8,019,619 B2 | 9/2011 | Ghouri |
| 8,046,242 B1 | 10/2011 | daCosta et al. |
| 8,099,339 B1 | 1/2012 | Pinsonneault |
| 8,321,283 B2 | 11/2012 | Rowe, III et al. |
| 8,630,873 B1 | 1/2014 | Wiley, II et al. |
| 2001/0001014 A1 | 5/2001 | Glendon, III et al. |
| 2001/0032099 A1 | 10/2001 | Joao |
| 2001/0037216 A1 | 11/2001 | Oscar et al. |
| 2001/0037224 A1 | 11/2001 | Eldridge et al. |
| 2001/0041993 A1 | 11/2001 | Campbell |
| 2002/0002495 A1 | 1/2002 | Ullman |
| 2002/0035488 A1 | 3/2002 | Aquila et al. |
| 2002/0044043 A1 | 4/2002 | Chaco et al. |
| 2002/0049617 A1 | 4/2002 | Lencki et al. |
| 2002/0055856 A1 | 5/2002 | Adams |
| 2002/0065687 A1 | 5/2002 | Onoue |
| 2002/0087554 A1 | 7/2002 | Seelinger |
| 2002/0087583 A1 | 7/2002 | Morgan et al. |
| 2002/0111832 A1* | 8/2002 | Judge .................................. 705/3 |
| 2002/0120473 A1 | 8/2002 | Wiggins |
| 2002/0128883 A1 | 9/2002 | Harris |
| 2002/0133503 A1 | 9/2002 | Amar et al. |
| 2002/0138593 A1 | 9/2002 | Novak et al. |
| 2002/0175370 A1 | 11/2002 | Bockelman |
| 2002/0183979 A1 | 12/2002 | Wildman |
| 2002/0198831 A1 | 12/2002 | Patricelli et al. |
| 2003/0009357 A1 | 1/2003 | Pish |
| 2003/0009367 A1 | 1/2003 | Morrison |
| 2003/0028404 A1 | 2/2003 | Herron et al. |
| 2003/0050799 A1 | 3/2003 | Jay et al. |
| 2003/0074218 A1 | 4/2003 | Liff et al. |
| 2003/0074222 A1 | 4/2003 | Rosow et al. |
| 2003/0083903 A1 | 5/2003 | Myers |
| 2003/0120588 A1 | 6/2003 | Dodd et al. |
| 2003/0125986 A1 | 7/2003 | Collosi |
| 2003/0149594 A1 | 8/2003 | Beazley et al. |
| 2003/0149625 A1 | 8/2003 | Leonardi et al. |
| 2003/0154163 A1 | 8/2003 | Phillips et al. |
| 2003/0229540 A1 | 12/2003 | Algiene |
| 2004/0006490 A1 | 1/2004 | Gingrich et al. |
| 2004/0019464 A1 | 1/2004 | Martucci et al. |
| 2004/0039599 A1 | 2/2004 | Fralic |
| 2004/0046020 A1 | 3/2004 | Andreasson et al. |
| 2004/0049422 A1 | 3/2004 | Mortimer |
| 2004/0054657 A1 | 3/2004 | Takeyama |
| 2004/0073457 A1 | 4/2004 | Maas et al. |
| 2004/0078234 A1 | 4/2004 | Tallal, Jr. et al. |
| 2004/0093242 A1 | 5/2004 | Cadigan et al. |
| 2004/0107117 A1 | 6/2004 | Denny |
| 2004/0111277 A1 | 6/2004 | Pearson et al. |
| 2004/0111291 A1 | 6/2004 | Dust et al. |
| 2004/0117323 A1 | 6/2004 | Mindala |
| 2004/0138921 A1 | 7/2004 | Broussard et al. |
| 2004/0148198 A1 | 7/2004 | Kalies |
| 2004/0153336 A1 | 8/2004 | Virdee et al. |
| 2004/0172281 A1 | 9/2004 | Stanners |
| 2004/0188998 A1 | 9/2004 | Henthorn |
| 2004/0249745 A1 | 12/2004 | Baaren |
| 2005/0015280 A1 | 1/2005 | Gabel et al. |

(56) References Cited

U.S. PATENT DOCUMENTS

| | | |
|---|---|---|
| 2005/0033604 A1 | 2/2005 | Hogan |
| 2005/0033610 A1 | 2/2005 | Cunningham |
| 2005/0060201 A1 | 3/2005 | Connely, III et al. |
| 2005/0065821 A1 | 3/2005 | Kalies |
| 2005/0086081 A1 | 4/2005 | Brock-Fisher |
| 2005/0090425 A1 | 4/2005 | Reardan et al. |
| 2005/0102169 A1 | 5/2005 | Wilson |
| 2005/0125292 A1 | 6/2005 | Kassab et al. |
| 2005/0154627 A1 | 7/2005 | Zuzek et al. |
| 2005/0171815 A1 | 8/2005 | Vanderveen |
| 2005/0187793 A1 | 8/2005 | Myles |
| 2005/0197862 A1 | 9/2005 | Paterson et al. |
| 2005/0240473 A1 | 10/2005 | Ayers, Jr. et al. |
| 2005/0288972 A1 | 12/2005 | Marvin et al. |
| 2006/0015518 A1 | 1/2006 | Eletreby et al. |
| 2006/0020514 A1 | 1/2006 | Yered |
| 2006/0026041 A1 | 2/2006 | Ullman |
| 2006/0085230 A1 | 4/2006 | Brill et al. |
| 2006/0095270 A1* | 5/2006 | Somerville ............... 705/1 |
| 2006/0149587 A1 | 7/2006 | Hill, Sr. et al. |
| 2006/0149784 A1 | 7/2006 | Tholl et al. |
| 2006/0184391 A1 | 8/2006 | Barre et al. |
| 2006/0224415 A1 | 10/2006 | Hudson et al. |
| 2006/0229915 A1 | 10/2006 | Kosinski et al. |
| 2006/0247948 A1 | 11/2006 | Ellis et al. |
| 2006/0259363 A1 | 11/2006 | Jhetam et al. |
| 2006/0265245 A1 | 11/2006 | McCallie et al. |
| 2006/0271398 A1 | 11/2006 | Belcastro |
| 2006/0271402 A1* | 11/2006 | Rowe et al. ............... 705/2 |
| 2006/0271405 A1 | 11/2006 | Cipolle et al. |
| 2006/0287886 A1 | 12/2006 | Kitazawa |
| 2007/0005402 A1 | 1/2007 | Kennedy et al. |
| 2007/0050209 A1 | 3/2007 | Yered |
| 2007/0088576 A1 | 4/2007 | de Beus et al. |
| 2007/0124177 A1 | 5/2007 | Engleson et al. |
| 2007/0136100 A1 | 6/2007 | Daugherty et al. |
| 2007/0162303 A1 | 7/2007 | Wiley et al. |
| 2007/0179957 A1 | 8/2007 | Gibson et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2008/0126117 A1 | 5/2008 | Miller et al. |
| 2008/0313103 A1 | 12/2008 | Burns et al. |
| 2009/0048864 A1 | 2/2009 | Kozlowski et al. |
| 2009/0222289 A1* | 9/2009 | Helmus et al. ............... 705/3 |
| 2009/0313039 A1 | 12/2009 | Cedergreen |
| 2010/0180223 A1* | 7/2010 | Speier ............... 715/771 |
| 2010/0324936 A1 | 12/2010 | Vishnubhatla et al. |

FOREIGN PATENT DOCUMENTS

| | | | |
|---|---|---|---|
| WO | 9106917 | A1 | 5/1991 |
| WO | 9503569 | A3 | 2/1995 |
| WO | 9725682 | A1 | 7/1997 |
| WO | 9850871 | A1 | 11/1998 |
| WO | 0039737 | A1 | 7/2000 |
| WO | 2007025295 | A2 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-32. vol. 63, Issue 1, USA.

Anonymous, TechRx Announces Successful Beta Deployment of T-Rex. PR Newswire. May 13, 2002.

"Two automatic identification technology, neither new in the sense if being recent developments . . . " Patient Safety & Quality Healthcare [Online] Aug. 2005. URL: http://www.awarix.com.

"Subnotebooks, Phones, and More. St. Vincent's Gets on Track." Mobile Health Data [Online], Nov. 19, 2004. URL:: http://www.awarix.com.

"Coping with Information Overload." The News Source for Healthcare Information Technology [Online] Nov. 2004. URL: http://www.awarix.com.

"St. Vincent's first to use Birmingham startup's information system." The Birmingham News [Online] Apr. 11, 2005. URL: http://www.awarix.com.

"St. Vincent's is Digital Flagship" D. Lockridge; Birmingham Medical News [Online] Sep. 2005. URL: http://www.awarix.com.

Non-Final Office Action for U.S. Appl. No. 11/441,554 mailed Nov. 24, 2009.

Non-Final Office Action for U.S. Appl. No. 11/608,068 mailed Jan. 11, 2010.

Final Office Action for U.S. Appl. No. 11/608,068 mailed May 10, 2010.

Final Office Action for U.S. Appl. No. 11/441,554 mailed May 11, 2010.

Non-Final Office Action for U.S. Appl. No. 11/441,554 mailed Oct. 13, 2010.

Final Office Action for U.S. Appl. No. 11/441,554 mailed Mar. 17, 2011.

Non-Final Office Action for U.S. Appl. No. 12/713,945 mailed Dec. 20, 2011.

Non-Final Office Action for U.S. Appl. No. 12/714,003 mailed Jan. 20, 2012.

Final Office Action for U.S. Appl. No. 13/435,241 mailed Dec. 6, 2012.

Point-of-Care Partners, "ePrescribing: Shapshot, Direction and Impact on Pharma" Bio/Phamaceutical Health Records and Data Summit; Oct. 22, 2007.

Cote, Bryan; "Adoption of e-prescribing yields surprising benefits to practices," Oncology business review, May 2009.

McKesson, "eScript" Mar. 2009.

Non-Final Office Action for U.S. Appl. No. 12/980,999 mailed Mar. 7, 2013.

Final Office Action for U.S. Appl. No. 13/435,245 mailed Sep. 24, 2012.

Final Office Action for U.S. Appl. No. 13/435,255 mailed Sep. 25, 2012.

Non-Final Office Action for U.S. Appl. No. 11/608,068 mailed Apr. 12, 2012.

Final Office Action for U.S. Appl. No. 12/713,945 mailed May 2, 2012.

Final Office Action for U.S. Appl. No. 12/714,003 mailed Jun. 12, 2012.

Non-Final Office Action for U.S. Appl. No. 13/435,255 mailed Jul. 2, 2012.

Non-Final Office Action for U.S. Appl. No. 11/608,068 mailed Jun. 17, 2013.

Final Office Action for U.S. Appl. No. 12/980,999 mailed Jun. 18, 2013.

Notice of Allowance for U.S. Appl. No. 13/435,255 mailed Sep. 3, 2013.

Non-Final Office Action for U.S. Appl. No. 13/435,245 mailed Jul. 19, 2012.

Notice of Allowance for U.S. Appl. No. 11/441,554 mailed Aug. 21, 2012.

Advisory Action for U.S. Appl. No. 12/713,945 mailed Sep. 4, 2012.

Final Office Action for U.S. Appl. No. 12/714,003 mailed Sep. 12, 2012.

Non-Final Office Action for U.S. Appl. No. 12/714,003 mailed Mar. 25, 2014.

\* cited by examiner

SYSTEMS AND METHODS FOR PROVIDING NOTIFICATIONS OF AVAILABILITY OF GENERIC DRUGS OR PRODUCTS

FIELD OF THE INVENTION

Aspects of the invention relate generally to healthcare transactions, and more particularly, to providing notifications of availability of generic drugs or products responsive to healthcare transactions.

BACKGROUND OF THE INVENTION

Generic versions of brand drugs can become available once the exclusivity periods expire for the branded drugs. However, retail pharmacies or patients may not be aware that these generic versions will soon be released. As such, there may be a delay after the generic release before the pharmacy realizes that the generic version is available, thereby resulting in profit loss to the pharmacy and higher costs to the patient. Therefore, a need exists for systems and methods for providing notifications of availability of generic drugs or products.

BRIEF DESCRIPTION OF THE INVENTION

Some or all of the above needs and/or problems may be addressed by certain embodiments of the invention. Embodiments of the invention may include systems and methods for providing notifications of availability of generic drugs or products. In one embodiment, a computer-implemented method for providing notifications of availability of generic drugs or products. The method may include receiving, from a healthcare provider computer, a healthcare claim transaction request that identifies a product for a patient; determining that the product identified by the healthcare claim transaction request is a non-generic product or a branded product; determining that a generic equivalent for the product identified by the healthcare claim transaction request will become available on a future date; generating a generic notification message indicating the availability of a generic equivalent for the product on the future date; and delivering or directing a delivery of the generic notification message. It is appreciated that the above operations can be performed by one or more computers associated with a service provider.

In accordance with another embodiment of the invention, a system for providing notifications of availability of generic drugs or products. The system may include at least one memory operable to store computer-executable instructions, and at least one processor configured to access the at least one memory. The at least one processor may be further configured to execute the computer-executable instructions to: receive, from a healthcare provider computer, a healthcare claim transaction request that identifies a product for a patient; determine that the product identified by the healthcare claim transaction request is a non-generic product or a branded product; determine that a generic equivalent for the product identified by the healthcare claim transaction request will become available on a future date; generate a generic notification message indicating the availability of generic equivalent for the product on the future date; and deliver or direct a delivery of the generic notification message.

Additional systems, methods, apparatus, features, and aspects may be realized though the techniques of various embodiments of the invention. Other embodiments and aspects of the invention are described in detail herein with reference to the description and to the drawings and are considered a part of the claimed invention.

BRIEF DESCRIPTION OF THE DRAWINGS

Reference will now be made to the accompanying drawings, which are not necessarily drawn to scale, and wherein.

DETAILED DESCRIPTION

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention may include systems and methods for providing notifications of availability of generic drugs or products. In this regard, the notifications may be delivered to a pharmacy, a healthcare provider, a patient, or any other recipient. In certain embodiments, a healthcare transaction request, such as a healthcare claim transaction request or an electronic prescription order may be received from a healthcare provider computer. The healthcare transaction request may be associated with one or more drugs or other products that are being prescribed or provided to a customer or patient by a healthcare provider such as a physician or a pharmacy. A drug or product associated with the healthcare transaction request may be identified, for example, by identifying and/or analyzing a National Drug Code (NDC), Universal Product Code (UPC), or a SKU number included in the healthcare transaction request. A determination may then be made as to whether the drug or product identified by the healthcare transaction request is a generic drug or product or a non-generic/branded drug or product. If a non-generic/branded drug or product is identified, then a determination can be made as to whether a generic equivalent will become available on a future date, perhaps within a predetermined time period from a current date of the healthcare transaction request. If the generic equivalent will become available, perhaps within the predetermined time period from the current date of the healthcare transaction request, then a generic notification message may be generated. The generic notification message may indicate the upcoming availability of the generic equivalent. The generic notification message can also optionally include additional information about the generic equivalent, including an expected date of availability and/or pricing information. The generic notification message may be delivered to a pharmacy (e.g., to the pharmacy as one response to the new healthcare transaction, fax, email, printer, voice message, paper mailing, etc.), a healthcare provider (e.g., fax, email, printer, voice message, paper mailing, etc.), a patient (e.g., email or other Internet message, cellular text message, fax, voice message, paper mailing, etc.).

System Overview

Figure 1:
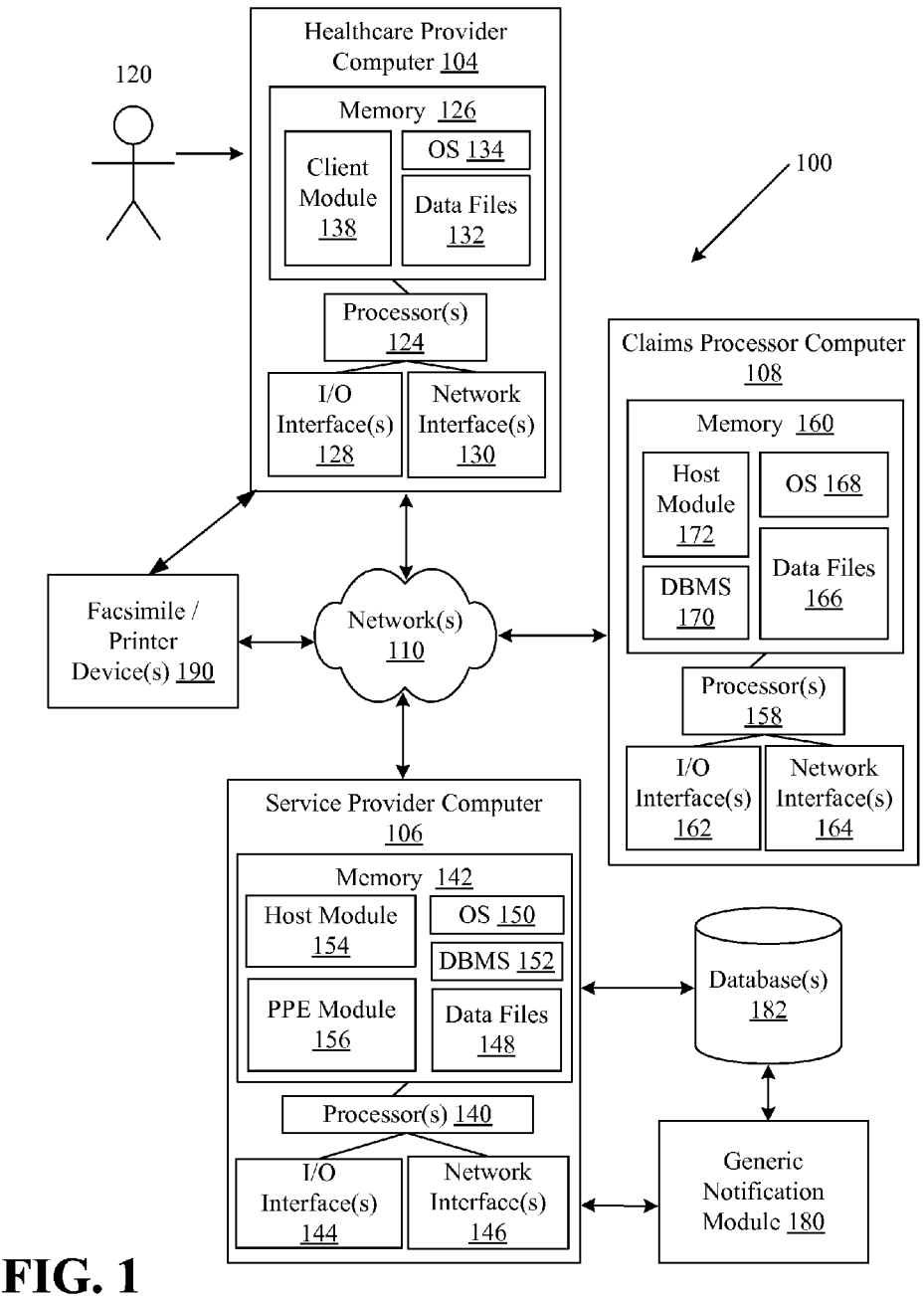
FIG. 1 illustrates an example overview of a system for providing notifications of availability of generic drugs or products, according to an example embodiment of the invention.

An example system 100 for providing notifications of availability of generic drugs or products will now be described illustratively with respect to FIG. 1. As shown in FIG. 1, the system 100 may include at least one healthcare provider computer 104, at least one service provider computer 106, and at least one claims processor computer 108. As desired, each of the healthcare provider computer 104, service provider computer 106, and/or claims processor computer 108 may include one or more processing devices that may be configured for accessing and reading associated computer-readable media having stored thereon data and/or computer-executable instructions for implementing the various methods of the invention.

Additionally, in certain embodiments, the service provider computer 106 may include or otherwise be in communication with a generic notification module 180 or generic notification application, which may access and/or be in communication with one or more suitable data storage devices, 182. The generic notification module 180 may receive information associated with a healthcare claim transaction, and the generic notification module 180 may identify a drug or other product associated with the received healthcare claim transaction. The generic notification module 180 may then determine whether the product is a generic product or a branded/non-generic product. If it is determined that the product is a branded/non-generic product, then the generic notification module 180 may determine whether a generic equivalent will become available on a future date, perhaps within an acceptable amount of time from a current date of the healthcare transaction request. If a generic equivalent will become available on the future date, perhaps within the acceptable amount of time from the current date of the healthcare transaction request, then the generic notification module 180 may generate a notification of availability of the generic drug or product for delivery to a pharmacy, a healthcare provider, and/or a patient. Additionally, as desired, the generic notification module 180 may facilitate reporting and/or billing for the processing and/or evaluation conducted by the generic notification module 180.

Generally, network devices and systems, including one or more of the healthcare provider computer 104, service provider computer 106, and claims processor computer 108 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computer 104, service provider computer 106, and claims processor computer 108 may be in communication with each other via one or more networks, such as network 110, which as described below can include one or more separate or shared private and public networks, including the Internet or a publicly switched telephone network. Each of these components—the healthcare provider computer 104, service provider computer 106, and claims processor computer 108, and the network 110—will now be discussed in further detail.

The healthcare provider computer 104 may be associated with a healthcare provider, for example, a pharmacy, physician's office, hospital, etc. In certain embodiments, the healthcare provider may be associated with a group of healthcare providers, such as a pharmacy chain. The healthcare provider computer 104 may be any suitable processor-driven device that facilitates the processing of healthcare requests made by patients or consumers and the communication of information associated with healthcare transactions (e.g., claim requests and/or electronic prescription orders) to the service provider computer 106, such as a server computer, a mainframe computer, one or more networked computers, a desktop computer, a personal computer, a digital assistant, a personal digital assistant, a digital tablet, an Internet appliance, an application specific circuit, microcontroller, minicomputer, or any other processor-based device. In certain embodiments, the healthcare provider computer 104 may be a suitable point of sale device associated with a healthcare provider. The execution of the computer-implemented instructions by the healthcare provider computer 104 may form a special purpose computer or other particular machine that is operable to facilitate the processing of healthcare requests made by patients and the communication of information associated with healthcare transaction requests to a service provider computer 106. Additionally, in certain embodiments of the invention, the operations and/or control of the healthcare provider computer 104 may be distributed amongst several processing components.

In addition to having one or more processors 124, the healthcare provider computer 104 may include one or more memory devices 126, one or more input/output ("I/O") interface(s) 128, and one or more network interface(s) 130. The memory devices 126 may be any suitable memory devices, for example, caches, read only memory devices, random access memory devices, magnetic storage devices, removable storage devices, etc. The memory devices 126 may store data, executable instructions, and/or various program modules utilized by the healthcare provider computer 104, for example, data files 132, an operating system 134, and/or a client module 138. The data files 132 may include any suitable data that facilitates the receipt and/or processing of healthcare requests by the healthcare provider computer 104 and the generation and/or processing of healthcare transactions that are communicated to the service provider computer 106. For example, the data files 132 may include, but are not limited to, healthcare information and/or contact information associated with one or more patients, information associated with the service provider computer 106, information associated with one or more claims processors, and/or information associated with one or more healthcare claim transactions. The operating system (OS) 134 may be a suitable software module that controls the general operation of the healthcare provider computer 104. The OS 134 may also facilitate the execution of other software modules by the one or more processors 124, for example, the client module 138. The OS 134 may be, but is not limited to, Microsoft Windows®, Apple OSX™, Linux, Unix, or a mainframe operating system. The client module 138 may be an Internet browser or other software, including a dedicated program, for interacting with the service provider computer 106. For example, a user 120 such as a pharmacist or other pharmacy employee, may utilize the client module 138 in preparing and providing a prescription claim request to the service processor computer 106 for delivery to the appropriate claims processor computer 108 for adjudication or other coverage/benefits determination. As another example, a user 120, such as a physician, may utilize the client module 138 in preparing and providing an electronic prescription order to the service provider computer 106 for delivery to another healthcare provider computer 104 (e.g., pharmacy computer) for receipt by a pharmacy management system. The healthcare provider computer 104 may also utilize the client module 138 to retrieve or otherwise receive data, messages, or responses from the service provider computer 106 and/or other components of the system 100.

In operation, the healthcare provider computer 104 may receive information associated with a healthcare request for a patient. As one example, the healthcare provider computer 104 may receive a healthcare request (e.g., a prescription order) for a patient at a point of sale, such as in a pharmacy during a prescription fulfillment or at a physician's office during the provision of a healthcare service. As another example, the healthcare provider computer 104 may electronically receive a healthcare request (e.g., an electronic prescription order) from a physician computer, a patient computer, or other patient device. The healthcare provider computer 104 may generate a healthcare claim transaction request for the request and information associated with the healthcare claim transaction request may be communicated to the service provider computer 106.

The one or more I/O interfaces 128 may facilitate communication between the healthcare provider computer 104 and one or more input/output devices, for example, one or more user interface devices, such as, a display, keypad, control panel, touch screen display, remote control, microphone, etc. that facilitate user interaction with the healthcare provider computer 104. For example, the one or more I/O interfaces 128 may facilitate entry of information associated with a healthcare transaction or healthcare claim request by an employee 120 of a healthcare provider, such as a pharmacy employee. The one or more network interfaces 130 may facilitate connection of the healthcare provider computer 104 to one or more suitable networks, for example, the network 110 illustrated in FIG. 1. In this regard, the healthcare provider computer 104 may receive and/or communicate information to other network components of the system 100, such as the service provider computer 106.

According to one embodiment, the healthcare provider computer 104 can further include a facsimile/printing device 190 operative to receive and print one or more generic notification messages associated with the upcoming availability of a generic drug or product. For example, as described further below, the service provider computer 106 may, on occasion, transmit a facsimile or other printing command to the healthcare provider computer 104 and/or the facsimile/printing device 190 containing one or more generic notification messages. The transmission from the service provider computer 106 may be directly to the facsimile/printing device 190, such as may be accomplished via a network 110 (e.g., Internet, cellular network, wireless network, or any other similar network, etc.). In another embodiment, the transmission may be to the healthcare provider computer 104, which, in turn, communicates with and commands the facsimile/printing device 190 to provide the generic notification message. Although the term facsimile/printing device is used throughout this description, it is appreciated that any other device operable to receive and print or generate a display of the notification message may be included within the scope of a facsimile/printing device 190. Examples of other devices include, but are not limited to, a mobile device (e.g., cellular telephone, personal digital assistant, personal information device, etc.), a personal computer, a computer kiosk, or any other handheld or mobile devices.

With continued reference to FIG. 1, the service provider computer 106 may include, but is not limited to, any suitable processor-driven device that is configured for receiving, processing, and fulfilling requests from the healthcare provider computer 104 and/or claims processor computer 108 relating to prescription, pharmacy, benefits, and/or healthcare transactions and/or other activities. In certain embodiments, the service provider computer 106 may be a switch/router that routes healthcare claim transactions and/or other healthcare requests. For example, the service provider computer 106 may route billing requests and/or prescription claim requests (also referred to as "healthcare claim requests") communicated from the healthcare provider computer 104 to a claims processor computer 108, such as a pharmacy benefits manager (PBM), an insurer, a government payor, or a claims clearinghouse. Likewise, the service provider computer 106 may also route electronic prescription orders communicated from a healthcare provider computer 104 (e.g., physician computer) to another healthcare provider computer 104 (e.g., a pharmacy computer) for receipt into a pharmacy management system. In certain embodiments, the service provider computer 106 may include a suitable host server, host module, or other software that facilitates the receipt of a healthcare transaction request from a healthcare provider computer 104 and/or the routing of the received healthcare transaction request to a claims processor computer 108. Any number of healthcare provider computers and/or claims processor computers may be in communication with the service provider computer 106 as desired in various embodiments of the invention.

The service provider computer 106 may include any number of special purpose computers or other particular machines, application specific circuits, microcontrollers, personal computers, minicomputers, mainframe computers, servers, networked computers, and/or other processor driven devices. In certain embodiments, the operations of the service provider computer 106 may be controlled by computer-executed or computer-implemented instructions that are executed by one or more processors associated with the service provider computer 106 to form a special purpose computer or other particular machine that is operable to facilitate the receipt, routing, and/or processing of healthcare transaction requests. The one or more processors that control the operations of the service provider computer 106 may be incorporated into the service provider computer 106 and/or in communication with the service provider computer 106 via one or more suitable networks. In certain embodiments of the invention, the operations and/or control of the service provider computer 106 may be distributed amongst several processing components.

Similar to the healthcare provider computer 104, the service provider computer 106 may include one or more processors 140, one or more memory devices 142, one or more input/output ("I/O") interface(s) 144, and one or more network interfaces 146. The one or more memory devices 142 may be any suitable memory devices, for example, caches, read only memory devices, random access memory devices, magnetic storage devices, removable memory devices, etc. The one or more memory devices 142 may store data, executable instructions, and/or various program modules utilized by the service provider 106, for example, data files 148, an operating system ("OS") 150, the host module 154, a pre- and post-edit (PPE) module 156, and a database management system ("DBMS") 152 to facilitate management of data files 148 and other data stored in the memory devices 142 and/or one or more databases 182. The OS 150 may be, but is not limited to, Microsoft Windows®, Apple OSX™, Linux, Unix, or a mainframe operating system.

The PPE module 156 may be operable to perform one or more pre-edits on a received healthcare transaction request prior to routing or otherwise communicating the received healthcare transaction request to a suitable claims processor computer 108 (for a claim request) or healthcare provider computer 104 (for an electronic prescription order). Additionally, the PPE module 156 may be operable to perform one or more post-edits on an adjudicated reply or response that is received from a claims processor computer 108 (or alternatively, a healthcare provider computer 104) for a healthcare claim transaction prior to routing the adjudicated reply to the healthcare provider computer 104. A wide variety of different pre-edits and/or post-edits may be performed as desired in various embodiments of the invention. In certain embodiments, the generic notification module 180 may be incorporated into the PPE module 156 and/or in communication with the PPE module 156.

According to an embodiment of the invention, the data files 148 may store healthcare transaction records associated with communications received from various healthcare provider computers 104 and/or various claims processor computers 108. The data files 148 may also store any number of suitable routing tables that facilitate determining the destination of communications received from a healthcare provider computer 104 or claims processor computer 108. The host module 154 may receive, process, and respond to requests from the client module 138 of the healthcare provider computer 104, and may further receive, process, and respond to requests of the host module 172 of the claims processor computer 108. The service provider computer 106 may include additional program modules for performing other processing methods described herein. Those of ordinary skill in the art will appreciate that the service provider computer 106 may include alternate and/or additional components, hardware or software without departing from example embodiments of the invention.

A generic notification module 180 or generic notification application may also be operative with the service provider computer 106. The generic notification module 180 may include computer-executable instructions for processing healthcare claim transactions in order to determine whether a generic notification message is to be generated for delivery to a pharmacy, healthcare provider, and/or patient. In certain embodiments, the generic notification module 180 may be a pre-edit service that is performed for a healthcare transaction request. If the generic notification service is enabled for a healthcare provider associated with the healthcare provider computer 104, then the generic notification module 180 may process a received healthcare transaction request in order to determine whether a generic notification message is to be generated for delivery.

In operation, the generic notification module 180 may receive information associated with a healthcare transaction request. The generic notification module 180 may identify one or more drugs or other products associated with or included in the received healthcare transaction request. A product may be identified, based at least in part, on product information included in the healthcare transaction request, such as NDC, UPC, or SKU information. For an identified product, the generic notification module 180 may determine whether the product is a branded/non-generic product, for example, by comparing a product identifier to one or more pre-stored identifiers for branded/non-generic products. If a product is determined to be a branded/non-generic product, then the generic notification module 180 may determine whether a generic equivalent will become available on a future date, perhaps within an acceptable amount of time from a current date of the healthcare claim transaction. For example, the generic notification module 180 may determine whether the generic equivalent will be available within 30 days, 90 days, or another predetermined amount of time from a current date of the healthcare transaction in order to ensure that any generated generic notification message will be reasonably timely to the recipient. If a generic equivalent will become available on the future date, perhaps within the acceptable amount of time from the current date of the healthcare transaction request, then the generic notification module 180 may trigger or generate a rejection for the healthcare transaction request. The rejection response can include a notification of availability of the generic drug or product for delivery to a pharmacy, a healthcare provider, and/or a patient. In an alternative embodiment, the generic notification message can be delivered without requiring a rejection for the healthcare transaction request. For example, the generic notification message can be delivered to a pharmacy, a healthcare provider, and/or a patient via a variety of electronic and non-electronic communication means as described herein.

In certain embodiments, the generic notification module 180 may identify one or more rules or parameters that are applicable for processing a healthcare transaction request. For example, the generic notification module 180 may identify one or more applicable rules or parameters based upon an identity of the healthcare provider that submitted the transaction request or a group of healthcare providers (e.g., a pharmacy chain) in which the healthcare provider is included. The identified rules may include rules associated with which products are being targeted for the generic notification service, as well as rules regarding the format (e.g., template, etc.), protocol (e.g., type of communication medium, etc.), or parameters (e.g., timing, etc.) for generic notification message delivery. Additionally, as desired, the identified rules may include rules associated with various edits and/or processing steps to be performed on a healthcare transaction request by the generic notification module 180. A wide variety of different edits may be performed as desired in various embodiments of the invention.

Additionally, as desired, the generic notification module 180 may store information associated with the healthcare transaction request in the data storage devices 182. For example, the generic notification module 180 may store the healthcare transaction request, information extracted from the healthcare transaction request, information associated with the rules applied to the healthcare transaction request, information associated with the results of the processing or evaluation of the healthcare transaction request, and/or information associated with identified or triggered rejections. In certain embodiments, the stored information may be utilized for billing and/or reporting purposes.

The data storage devices 182 may be operable to store information associated with various rules and/or edits that may be utilized by the generic notification module 180 to process healthcare claim transactions. For example, rules may be received from one or more other components of the system 100, such as the healthcare provider computer 104, and/or the claims processor computer 108, and at least a portion of the received rules may be stored. Additionally, the data storage devices 182 may be operable to store information associated with healthcare transaction requests and/or processing performed by the generic notification module 180. In certain embodiments, the data storage devices 182 may additionally store billing information associated with the healthcare transaction requests and/or reports associated with the healthcare transaction requests and/or processing of the healthcare transaction requests. The data storage devices 182 may be accessible by the generic notification module 180 and/or the service provider computer 106.

In certain embodiments, the generic notification module 180 and/or the service provider computer 106 may be operable to generate one or more reports associated with processed healthcare transaction requests. A wide variety of different types of reports may be generated as desired in various embodiments of the invention. Additionally, a wide variety of different information may be incorporated into generated reports, including but not limited to, a number of times the generic notification module 180 was invoked for a healthcare provider or group of healthcare providers (e.g., a pharmacy chain), information associated with the results of various processing performed by the generic notification module 180, date information and/or date range information associated with the processed healthcare transaction requests, any financial information associated with the healthcare transaction requests (e.g., claim request), and/or billing information associated with the invocation of the generic notification module 180 for the healthcare transaction requests. Reports may be sorted or formatted utilizing a wide variety of different criteria, parameters, and/or techniques. Additionally, the generic notification module 180 may communicate or direct the communication of generated reports to one or more other components of the system, for example, the healthcare provider computer 104 associated with a group of healthcare providers.

A wide variety of different techniques and/or software programs may be utilized to format a generated report. For example, a report may be formatted as a comma-separated-value (csv) file, as a spreadsheet file, as a word processor file, as a text file, etc. Additionally, a wide variety of different communication techniques may be utilized to communicate a report to the recipient, including but not limited to, email, short message service (SMS) messaging, other electronic communications, snail mail, etc. A report may be pushed to a recipient by the generic notification module 180 or other reporting module, or, alternatively pulled from the generic notification module 180 by a recipient submitting a request for one or more reports. Additionally, in certain embodiments, a report may be made available for download from an appropriate web site or server, such as a web site hosted by the service provider computer 106.

The operations of the generic notification module 180 and/or the data storage devices 182 are described in greater detail below with reference to FIGS. 2-4.

With continued reference to the service provider computer 106, the one or more I/O interfaces 144 may facilitate communication between the service provider computer 106 and one or more input/output devices, for example, one or more user interface devices, such as, a display, keypad, control panel, touch screen display, remote control, microphone, etc. that facilitate user interaction with the service provider computer 106. The one or more network interfaces 146 may facilitate connection of the service provider computer 106 to one or more suitable networks, for example, the network 110 illustrated in FIG. 1. In this regard, the service provider computer 106 may communicate with other components of the system 100.

With continued reference to FIG. 1, the claims processor computer 108 may be any suitable processor-driven device that facilitates receiving, processing, and/or fulfilling healthcare claim transactions and/or healthcare claim requests received from the service provider computer 106. For example, the claims processor computer 108 may be a processor-driven device associated with a pharmacy benefits manager (PBM), an insurer, a government payor, or a claims clearinghouse. As desired, the claims processor computer 108 may include any number of special purpose computers or other particular machines, application specific circuits, microcontrollers, personal computers, minicomputers, mainframe computers, servers, and the like. In certain embodiments, the operations of the claims processor computer 108 may be controlled by computer-executed or computer-implemented instructions that are executed by one or more processors associated with the claims processor computer 108 to form a special purpose computer or other particular machine that is operable to facilitate the receipt, processing, and/or fulfillment of healthcare claim transaction requests received from the service provider computer 106. The one or more processors that control the operations of the claims processor computer 108 may be incorporated into the claims processor computer 108 and/or in communication with the claims processor computer 108 via one or more suitable networks. In certain embodiments of the invention, the operations and/or control of the claims processor computer 108 may be distributed amongst several processing components.

Similar to other components of the system 100, the claims processor computer 108 may include one or more processors 158, one or more memory devices 160, one or more input/output ("I/O") interface(s) 162, and one or more network interfaces 164. The one or more memory devices 160 may be any suitable memory devices, for example, caches, read only memory devices, random access memory devices, magnetic storage devices, removable memory devices, etc. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare claim transactions, for example, patient profiles, patient insurance information, other information associated with a patient, information associated with a healthcare provider, etc. The operating system (OS) 168 may be a suitable software module that controls the general operation of the claims processor computer 108. The OS 168 may also facilitate the execution of other software modules by the one or more processors 158, for example, the DBMS 170 and/or the host module 172. The OS 150 may be, but is not limited to, Microsoft Windows®, Apple OSX™, Linux, Unix, or a mainframe operating system. The DBMS 170 may be a suitable software module that facilitates access and management of one or more databases that are utilized to store information that is utilized by the claims processor computer 108 in various embodiments of the invention. The host module 172 may initiate, receive, process, and/or respond to requests, such as healthcare claim transactions or claim requests, from the host module 154 of the service provider 106. The claims processor computer 108 may include additional program modules for performing other pre-processing or post-processing methods described herein. Those of ordinary skill in the art will appreciate that the claims processor 108 computer may include alternate and/or additional components, hardware or software without departing from example embodiments of the invention.

The one or more I/O interfaces 162 may facilitate communication between the claims processor computer 108 and one or more input/output devices, for example, one or more user interface devices, such as, a display, keypad, control panel, touch screen display, remote control, microphone, etc. that facilitate user interaction with the claims processor computer 108. The one or more network interfaces 164 may facilitate connection of the claims processor computer 108 to one or more suitable networks, for example, the network 110 illustrated in FIG. 1. In this regard, the claims processor computer 108 may receive healthcare claim transactions and/or other communications from the service provider computer 106, and the claims processor computer 108 may communicate information associated with processing claim transactions to the service provider.

The network 110 may include any telecommunication and/or data network, whether public, private, or a combination thereof, including a local area network, a wide area network, an intranet, the Internet, intermediate hand-held data transfer devices, and/or any combination thereof and may be wired and/or wireless. The network 110 may also allow for real-time, off-line, and/or batch transactions to be transmitted between or among the healthcare provider computer 104, the service provider computer 106, and the claims processor computer 108. Due to network connectivity, various methodologies as described herein may be practiced in the context of distributed computing environments. Although the service provider computer 106 is shown for simplicity as being in communication with the healthcare provider computer 104 or the claims processor computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment of the invention. For example, the service provider computer 106 may form the basis of network 110 that interconnects the healthcare provider computer 104 and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one embodiment, the service provider computer 106 (or other computer) may be implemented as a specialized processing machine that includes hardware and/or software for performing the methods described herein. In addition, at least a portion of the processor and/or processing capabilities of the service provider computer 106 and/or the generic notification module 180, may be implemented as part of the claims processor computer 108. Accordingly, embodiments of the invention should not be construed as being limited to any particular operating environment, system architecture, or device configuration.

Operational Overview

Figure 2:
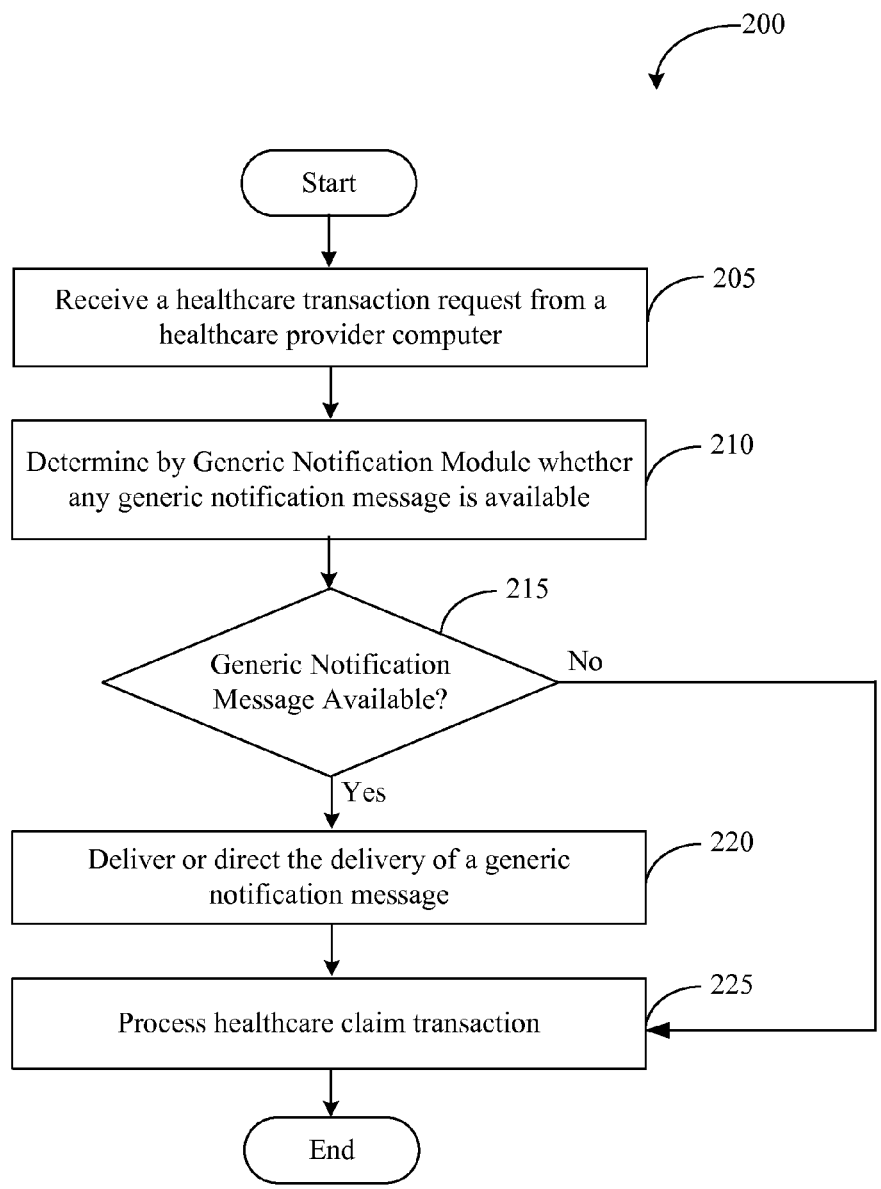
FIG. 2 illustrates a high-level overview of an example process for providing notifications of availability of generic drugs or products, according to an example embodiment of the invention.

FIG. 2 illustrates a high-level overview of an example process 200 for providing notifications of availability of generic drugs or products, according to an example embodiment of the invention. At block 205, a healthcare provider computer 104 (e.g., a pharmacy computer, a physician computer, etc.) may generate a healthcare transaction request, such as a healthcare claim request (e.g., a prescription claim request) or an electronic prescription order (e.g., an E-script). The generated healthcare transaction request may be communicated by the healthcare provider computer 104 to the service provider computer 106. According to an example embodiment of the invention, the healthcare transaction request may be in accordance with a version of a National Council for Prescription Drug Programs (NCPDP) Telecommunication or SCRIPT Standard, although other standards may be utilized as well.

If the healthcare transaction request is a healthcare claim request generated by a pharmacy computer, the request may include a Banking Identification Number (BIN) and/or a Processor Control Number (PCN) for identifying a particular claims processor computer or payer, such as the claims processor computer 108 illustrated in FIG. 1, as a destination for the healthcare claim transaction request. In addition, the healthcare claim request may also include information relating to the patient, payor, prescriber, healthcare provider, and/or the prescribed or administered drug or product. As an example, the healthcare claim request received by the service provider computer 106 may include one or more of the following information:

Payor ID/Routing Information
    BIN Number (i.e. Banking Identification Number) and/or Processor Control Number (PCN) that designates a destination of the healthcare claim transaction
Patient Information
    Name (e.g., Patient Last Name, Patient First Name, etc.)
    Date of Birth of Patient
    Age of Patient
    Gender
    Patient Address (e.g., Street Address, Zip Code, etc.)
    Patient Contact Information (e.g., Patient Telephone Number, email address, etc.)
    Patient ID or other identifier
Insurance/Coverage Information
    Cardholder Name (e.g., Cardholder First Name, Cardholder Last Name)
    Cardholder ID and/or other identifier (e.g., person code)
    Group ID and/or Group Information
    State Payor Information
    Prescriber Information
    Primary Care Provider ID or other identifier (e.g., NPI code)
    Primary Care Provider Name (e.g., Last Name, First Name)
    Prescriber ID or other identifier (e.g., NPI code, DEA number)
    Prescriber Name (e.g., Last Name, First Name)
    Prescriber Contact Information (e.g., Telephone Number)
    Pharmacy or other Healthcare Provider Information (e.g., store name, chain identifier, etc.)
    Pharmacy or other Healthcare Provider ID (e.g., National Provider Identifier (NPI) code)
Claim Information
    Drug or product information (e.g., National Drug Code (NDC))
    Prescription/Service Reference Number
    Date Prescription Written
    Quantity Dispensed
    Number of Days Supply
    Diagnosis/Condition
    Pricing information for the drug or product (e.g., network price, Usual & Customary price)
    One or more NCPDP Message Fields One or more Drug Utilization (DUR) Codes
One or more Dispense as Written (DAW) Codes or other DAW information
Date of Service.

Similarly, if the healthcare transaction request is an electronic prescription order generated by a physician/prescriber/hospital/clinic computer, then the request may include one or more of the following healthcare transaction information: a pharmacy identifier for identifying another healthcare provider computer 104 (e.g., a pharmacy computer) as a destination of the electronic prescription order; prescriber/healthcare provider information; prescribed drug or product information; diagnosis/ailment information; and/or patient information. For example, prescriber/healthcare provider information may include a name and/or contact information (e.g., address and/or telephone number) and an identifier for the prescriber (e.g., a National Provider Identifier (NPI) code or Drug Enforcement Administration (DEA) number). The prescribed drug or product information may include a name of a prescribed drug or product, a drug/product identifier (e.g., a National Drug Code (NDC)), or other information such as quantity, refills, form (e.g., tablet, gel, etc.), dosage instructions, and/or date for the prescription. The diagnosis/ailment information may include certain codes or identifiers to identify the condition(s) that the service or product is being prescribed to treat. The patient information may include a name and/or contact information for the patient, as well as other patient information such as a date of birth (DOB).

At block 210, the service provider computer 106, perhaps in accordance with an operation of the generic notification module 180, may determine whether any generic notification messages are available based upon the received healthcare transaction request. In general, block 210 may involve identifying whether the drug or product of the healthcare transaction request is a generic, and if not, whether a generic equivalent will be available on a future date, perhaps within an acceptable amount of time (e.g., 30 days, 60 days, or another predetermined amount of time) from a current date of the healthcare transaction request. According to an example embodiment of the invention, information from one or more generic manufacturers or distributors regarding the future date(s) of availability of generic equivalents to one or more branded or non-generic drugs or products may be stored in and accessible from database 182 or from memory 142. Likewise, the information regarding future date(s) of availability of generic equivalents may be stored in a table that cross-references the corresponding identification of branded/non-generic drugs (e.g., NDC, SKU, UPC). It will be appreciated that the table may be specific for a particular healthcare provider (e.g., a particular pharmacy location) or group or healthcare providers (e.g., a retail chain of pharmacies). Thus, there may be respective tables for respective healthcare providers, according to an example embodiment of the invention. Accordingly, block 210 may utilize the drug or product identifier of the healthcare transaction request, and optionally, information regarding the location where the drug or product is to be filled, in conjunction with the respective table to determine if any generic equivalents will become available on a future date. It will be appreciated that the information stored in the table could likewise be stored in other formats, such as a relational database format, a spreadsheet format, and the like.

If no generic notification messages are available at block 215, then processing may proceed to block 225, wherein the healthcare transaction request can be processed according to traditional processing. For example, for a healthcare claim request, the service provider computer 106 can communicate the request to an appropriate claims processor computer 108 (for a healthcare claim request) for adjudication or other benefits processing. The claims processor computer 108 can provide an adjudicated reply indicating a result of processing the healthcare claim request. The adjudicated reply can indicate whether the claim request was paid or rejected, and if paid, the covered amount and/or the patient responsibility amount (e.g., co-pay amount, co-insurance amount). Likewise, for an electronic prescription order, the service provider computer 106 can communicate the electronic prescription order to a healthcare provider computer 104 (e.g., a pharmacy computer) for receipt into the pharmacy management system. The healthcare provider computer 104 can provide a response that indicates whether the electronic prescription order was successfully accepted into the pharmacy management system. The response from either the claims processor computer 108 or the healthcare provider computer 104 is received by the service provider computer 106, which in turn, provides information from the received response to the healthcare provider computer 104 that originated the healthcare transaction request.

On the other hand, a generic notification message may be available at block 215, in which case processing may proceed to block 220. At block 220, the generic notification message may be delivered to a pharmacy, a healthcare provider, a patient, or virtually any other designated recipient. For example, the generic notification message may be delivered to a pharmacy or healthcare provider as a response to a particular healthcare transaction request. Yet further, in an example embodiment of the invention, the response may be a rejection response to the particular healthcare transaction request, wherein the rejection response includes or incorporates the generic notification message. However, in other example embodiments, the response may be an adjudicated reply, wherein the generic notification message is appended to the adjudicated reply, or otherwise included in a message field of the reply. It will also be appreciated that the generic notification message may also be delivered to the pharmacy, healthcare provider, or patient via email or other Internet message, fax, printer, voice message, paper mailing, or any other electronic or non-electronic communication means.

Following block 220 is block 225. At block 225, the healthcare transaction request may be processed. The processing may depend on how the generic notification message of block 220 is to be delivered. If the generic notification message is to be delivered as part of a rejection response to the healthcare transaction request, then the healthcare transaction request may be rejected, and the generic notification message may be included in a rejection response communicated to the healthcare provider computer 104. In another embodiment, if the healthcare transaction request is a healthcare claim request, the healthcare transaction request can be routed to the claims processor computer 108 for adjudication or benefits processing, and an adjudicated reply may be received by the service provider computer 106. The service provider computer 106 can then append or include the generic notification message with the adjudicated reply that is provided in the response to the healthcare provider computer 104. On the other hand, if the healthcare transaction request is an electronic prescription order, the healthcare transaction request can be routed to a physician/prescriber/hospital,/clinic computer, and a response (e.g., an acknowledgement response) can be received by the service provider computer. Similarly, the generic notification message may be appended to the received response and communicated to the healthcare provider computer 104. It will be appreciated that in some embodiments, the generic notification message can be delivered to the pharmacy, physician, and/or patient independently of the delivery of the response to the healthcare provider computer 104 or independently of the healthcare transaction network or associated protocol. In this case, the generic notification message can be delivered via email or other Internet message, fax, printer, voice message, paper mailing, or any other electronic or non-electronic communication means described herein.

The generic notification message may indicate that a generic equivalent will be available, perhaps on one or more particular future dates. Likewise, the generic notification message may likewise identify one or more pharmacy locations that may have the generic equivalent available on the one or more particular futures dates. In an example embodiment of the invention, the generic notification message may also indicate pricing information for the generic equivalent and/or any potential savings between the branded/non-generic drug or product and the generic equivalent. For example, the pricing information for the generic equivalent may be stored, perhaps in a table, along with the future date of availability in the database 182 or the memory 142 of the service provider computer 106. It will be appreciated that different pricing information may be available, depending on the particular claims processor computer 108 or pharmacy identified by the healthcare transaction request. For example, a particular pharmacy may anticipate charging a particular price for a generic equivalent, or a claims processor may be expected to cover a certain amount of a price for the generic equivalent, thereby leaving a particular patient responsibility amount. Any potential price savings can be determined by comparing the price or amount (e.g., patient responsibility amount) indicated by the healthcare transaction request and/or adjudicated reply, according to an example embodiment of the invention.

Figure 3A:
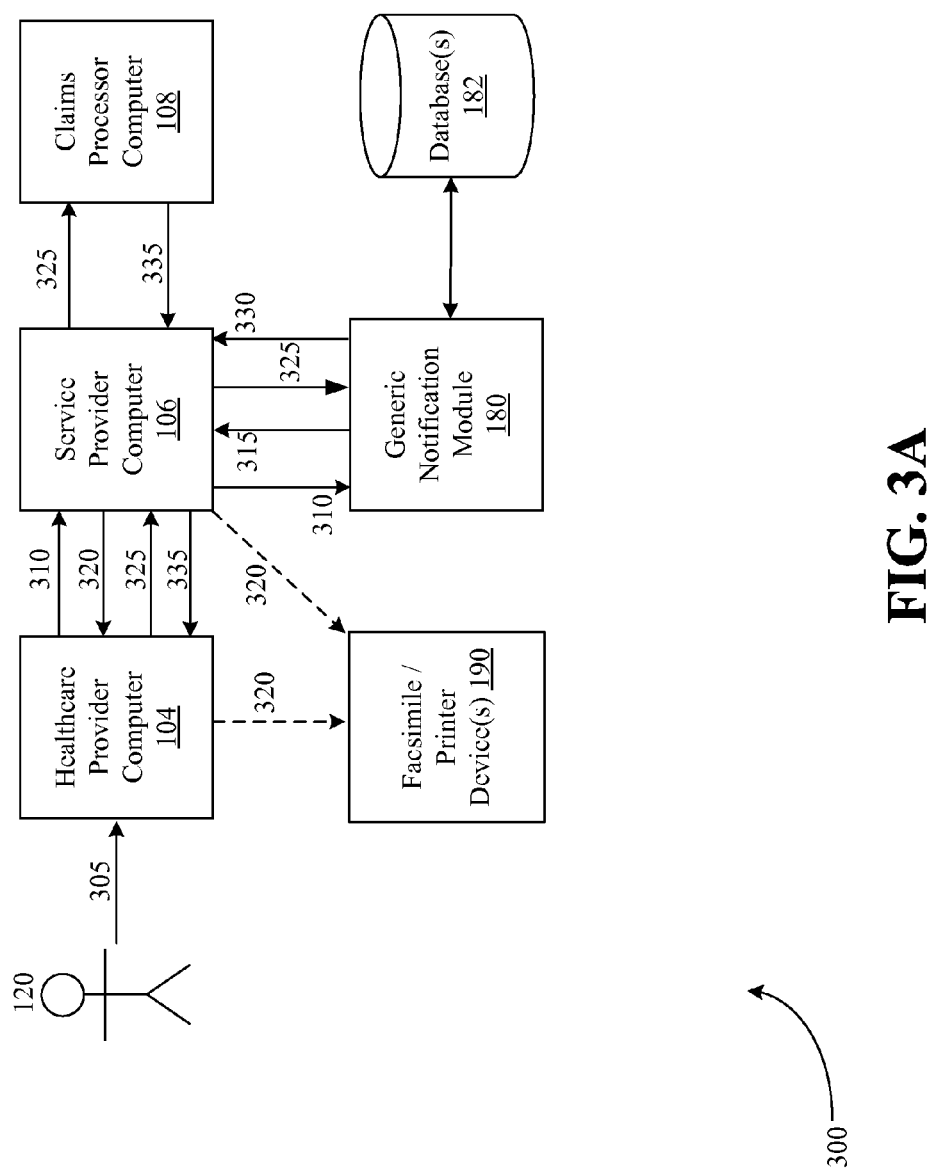
FIGS. 3A and 3B illustrate example block diagrams for providing notifications of availability of generic drugs or products in accordance for a healthcare claim transaction, according to illustrative embodiments of the invention.

FIG. 3A illustrates an example block diagram 300 for providing notifications of availability of generic drugs or products in accordance for a healthcare claim transaction, according to an example embodiment of the invention. The flow diagram of FIG. 3A will be discussed in conjunction with the example flow diagram 400 of FIG. 4

Figure 4:
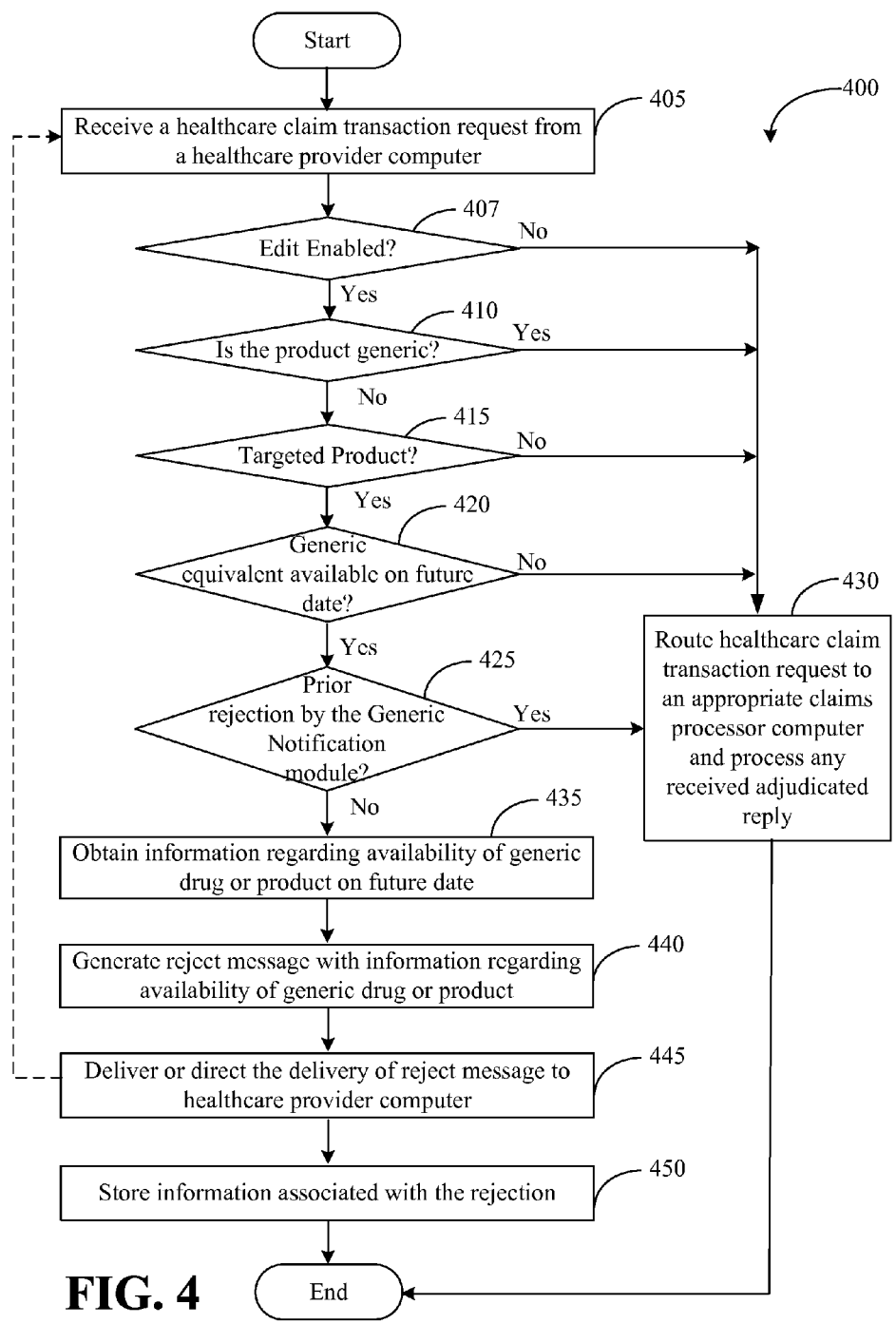
FIG. 4 is a flow chart of an example method for providing notifications of availability of generic drugs or products in accordance with a healthcare claim transaction, according to an illustrative embodiment of the invention.

With reference to FIGS. 3A and 4, a healthcare provider computer, such as the healthcare provider computer 104 illustrated in FIG. 1, may receive a healthcare request 305 (e.g., a prescription order) from a patient, such as a healthcare request 305 for a prescription drug or product. The healthcare request 305 may be received in-person or electronically as desired in various embodiments of the invention. For example, a patient may request a medication product at a pharmacy or physician's offices. As another example, a patient may communicate a healthcare request 305 to a healthcare provider computer 104 via one or more suitable network connections. For example, a purchase request for a product may be communicated to a healthcare provider computer 104 from a customer computer via a web portal hosted by the healthcare provider computer 104. Likewise, the healthcare request 305 may be received as an electronic prescription order from a physician/prescriber/hospital/clinic computer.

At block 405, the healthcare provider computer 104 may receive and process the request 205 to generate a healthcare claim transaction request 310, such as a healthcare claim request or a prescription claim request. The healthcare claim transaction request 310 may be communicated by the healthcare provider computer 104 to the service provider computer 106. According to an example embodiment of the invention, the healthcare claim transaction may be in accordance with a version of a National Council for Prescription Drug Programs (NCPDP) Telecommunication Standard, although other standards may be utilized as well. As desired, the healthcare claim transaction request 310 may include a Banking Identification Number (BIN) and/or a Processor Control Number (PCN) for identifying a particular claims processor computer or payer, such as the claims processor computer 108 illustrated in FIG. 1, as a destination for the healthcare claim transaction request 310. In addition, the healthcare claim transaction request 310 may also include information relating to the patient, payor, prescriber, healthcare provider, and/or the prescribed or administered drug or product, as described herein.

With continued reference to FIGS. 3A and 4, the service provider computer 106 may receive the healthcare claim transaction request 310 from the healthcare provider computer 104, and the service provider computer 106 may process the healthcare claim transaction request 310. As desired, the service provider computer 106 may perform one or more pre-edits on the healthcare claim transaction request 310. The pre-edits may verify, add, and/or edit information included in the healthcare claim transaction request 310 prior to the healthcare claim transaction request 310 being communicated to an appropriate claims processor computer 108. In certain embodiments, a determination may be made as to whether a generic notification edit is enabled for the healthcare claim transaction request 310, as illustrated by block 407. For example, a determination may be made as to whether a healthcare provider or group of healthcare providers associated with the transaction request 310 has enabled or activated a generic notification edit for use in processing healthcare claim transactions that are routed or otherwise communicated through the service provider computer 106. For example, the healthcare claim transaction request 310 may specify a pharmacy identifier that is then compared to a list of acceptable pharmacy identifiers for those pharmacies that have enabled or activated the generic notification edit.

If a generic notification edit is not activated or enabled at block 407 for processing the healthcare claim transaction request 310 and no rejections are triggered or generated by any other pre-edits performed for the request 310, then the healthcare claim transaction request 310 and/or a copy thereof may be routed or otherwise communicated by the service provider computer 106 to the appropriate claims processor computer 108 for adjudication, as provided by block 430. According to an example embodiment, the service provider 106 may utilize at least a portion of the information included in the healthcare claim transaction request 310, such as a BIN/PCN, to determine the appropriate claims processor computer 108 to route the healthcare claim transaction request 310 to. The service provider computer 106 may also include a routing table, perhaps stored in memory, for determining which claims processor computer 108 to route the healthcare claim transaction request 310 to. An adjudicated reply may be received by service provider computer 106 from the claims processor 108. The adjudicated reply typically indicates whether the claim was paid or rejected by the claims processor computer 108. If the claim was paid, then adjudicated reply typically further indicates financial coverage information, such as a covered amount and/or a patient responsibility amount (e.g., a co-pay amount and/or a con-insurance amount). The service provider computer 106 may optionally perform any post-edits prior to communicating the adjudicated reply to the healthcare provider computer.

If a generic notification edit is enabled at block 407 for processing the healthcare claim transaction request 310, then the healthcare claim transaction request 310, a copy of the request 310, and/or information included in the request 310 may be communicated to a suitable generic notification edit module, such as the generic notification module 180 shown in FIG. 1, for processing. At block 410, the generic notification module 180 may identify or determine one or more drugs or other products included in or associated with the healthcare claim transaction request 310. For example, the generic notification module 180 may identify one or more NDC, SKU, UPC, or other product identifiers (e.g., product names, etc.) included in the healthcare claim transaction request 310 in order to identify one or more products. Once a product is identified, the generic notification module 180 may determine whether the identified product is a generic product, for example, by comparing a product identifier to one or more pre-stored identifiers for generic products. If the identified product is a generic product, then no further processing is needed since a generic product is already identified by the healthcare claim transaction request 310. In this case, the generic notification module 180 may mark the healthcare claim transaction request 310 as an approved or acceptable transaction to facilitate routing or communication of the healthcare claim transaction request 310 to the claims processor computer 108 by the service provider computer 106 at block 430. As desired, the generic notification module 180 may communicate a message 315 indicating that the healthcare claim transaction request 310 is not affected by the generic notification edit, and the service provider computer 106 may route the healthcare claim transaction request 310 and/or perform additional processing on the healthcare claim transaction request 310 based upon the receipt of the message 315, as provided by block 430.

If, however, the identified product is not a generic product, but is instead a branded/non-generic product, then processing may proceed to block 415. At block 415, the generic notification module 180 may optionally determine whether the identified product is a targeted product. For example, the products that are targeted may be based the healthcare provider originating the healthcare claim transaction request 310 (e.g., based upon the service provider ID of the request 310). Indeed, there may be a list of targeted products (e.g., by product identifier) available for a particular healthcare provider. Indeed, certain healthcare providers (e.g., pharmacies) may have targeted products based upon their relationship with particular generic pharmaceutical manufacturers or distributers.

If the product is not determined to be a targeted product at block 415, then the generic notification module 180 may communicate a message 315 indicating that the healthcare claim transaction request 310 is not affected by the generic notification edit, and the service provider computer 106 may route the healthcare claim transaction request 310 and/or perform additional processing on the healthcare claim transaction request 310 based upon the receipt of the message 315, as provided by block 430.

On the other hand, the product may be determined to be a targeted product at block 415, and processing may proceed to block 420. At block 420, the generic notification module 415 may determine whether a generic equivalent to the targeted product will be available on a future date. To make this determination, the generic notification module 415 may access information from database 182 or memory 142 regarding the future date(s) of availability of generic equivalents to one or more branded or non-generic drugs or products may be accessible from database 182 or from memory 142. For example, the information regarding future date(s) of availability of generic equivalents may be stored in a table having corresponding cross references to identifications (e.g., NDC, SKU, UPC) of branded/non-generic drugs. It will be appreciated that the table may be specific for a particular healthcare provider (e.g., a particular pharmacy location) or group or healthcare providers (e.g., a retail chain of pharmacies), according to an example embodiment of the invention. Accordingly, block 420 may utilize the drug or product identifier of the healthcare transaction request, and optionally, information regarding the location where the drug or product is to be filled, in conjunction with a table to determine if any generic equivalents will become available on a future date. In addition, block 420 may further determine whether the future date of availability is within an acceptable amount of time from a current date associated with the healthcare claim transaction request 310. This amount of time may be, for example, within 30 days, 90 days, or another predetermined amount of time to ensure that any generic notification messages are received by the pharmacy, physician, patient, or other intended recipient in a timely manner or a manner that is likely to be relevant to the recipient. The predetermined amount of time may be configured by the service provider or the healthcare provider. Likewise, the predetermined amount of time may be based upon the intended recipient (e.g., a patient, a physician, etc.) of any generic notification messages.

If block 420 determines that no generic equivalent is available on a future date, or that the future date is not within the acceptable amount of time from a current date, then the generic notification module 180 may communicate a message 315 indicating that the healthcare claim transaction request 310 is not affected by the generic notification edit. Thus, at block 430, the service provider computer 106 may route the healthcare claim transaction request 310 and/or perform additional processing on the healthcare claim transaction request 310 based upon the receipt of the message 315.

On the other hand, block 420 may determine that a generic equivalent is available on a future date, perhaps within an acceptable amount of time from a current date associated with the healthcare claim transaction request 310. In this case, processing may proceed to block 425. At block 425, the generic notification module 180 may determine whether a prior rejection of a similar healthcare claim transaction has been recorded in a history file or record, which may be stored in the database 182 or memory 142. A prior rejection may be determined by matching one or more of the following information between the healthcare claim transaction request 310 and an entry in the history file or record: patient identifier, the drug or product identifier, healthcare provider identifier (e.g., pharmacy ID, prescribing physician ID, etc.), and/or date associated with the healthcare claim transaction. If a similar healthcare claim transaction has been identified as being previously rejected at block 425, perhaps within a particular time frame (e.g., past 1 day, 7 days, 14 days, etc.), then the generic notification module 180 may communicate a message 315 indicating that the healthcare claim transaction request 310 is not affected by the generic notification edit. Thus, at block 430, the service provider computer 106 may route the healthcare claim transaction request 310 and/or perform additional processing on the healthcare claim transaction request 310 based upon the receipt of the message 315.

On the other hand, if no similar healthcare claim transaction can be identified as being previously rejected, then processing may proceed to block 435. At block 435, the generic notification module 180 may obtain information regarding the availability of the generic equivalent on a future date. For example, the information regarding future date(s) of availability of generic equivalents may be stored in a table, perhaps stored in database 182 or memory 142, having the corresponding identification of branded/non-generic drugs (e.g., NDC, SKU, UPC). Thus, by matching the branded or non-generic drug identified by the healthcare claim transaction request 310 to a corresponding entry in a table, the information regarding the availability of a generic equivalent on a particular date may be obtained. In addition, the generic notification module 180 may optionally obtain pricing information regarding the generic equivalent, which may likewise be stored in the table in conjunction with the future availability date of the generic equivalent. It will be appreciated that different pricing information may be available, depending on the particular claims processor computer 108 or healthcare provider computer 104 identified by the healthcare claim transaction request 310.

At block 435, the generic notification module 180 may communicate a message 315 to the service provider computer 104. The message 315 may indicate that a generic equivalent is available, and may further optionally identify a future date on which the generic equivalent may be available at a particular pharmacy location. The message 315 may also indicate pricing information regarding the available generic equivalent.

Following block 435 is block 440. At block 440, the service provider computer 106 may generate one or more suitable messages 320 indicating a rejection of the healthcare claim transaction request 310. The message 320 may include one or more reasons for rejecting the healthcare claim transaction request 310, for example, an indication that a generic equivalent may be available in the future. Indeed, the message 320 may include similar information as provided from the message 315, including an indication that a generic equivalent is available, and optionally, information regarding a date of availability and/or pricing information for the generic equivalent.

At block 445, the service provider 106 may deliver or direct the delivery of the message 320 to the healthcare provider computer 104, perhaps as a response to the healthcare claim transaction request 310. In addition or in the alternative, a message 320 with the information regarding the availability of the generic equivalent may also be delivered to a facsimile/printer device 190. In an example embodiment of the invention, the message 320 may be delivered directly to the facsimile/printer device 190, or indirectly to the to the facsimile/printer device 190 via the healthcare provider computer 104. As an alternative to the facsimile/printer device 190, the message 320 can also be delivered to a mobile device (e.g., cellular telephone, personal digital assistant, personal information device, etc.), a personal computer, a computer kiosk, or any other handheld or mobile devices, as described herein.

At block 450, the service provider computer 106 and/or the generic notification module 180 may store, in a history file or record, an identification of the rejected healthcare claim transaction. As an example, the history file or record may include one or more of the following: patient identifier, the drug or product identifier, healthcare provider identifier (e.g., pharmacy ID, prescribing physician ID, etc.), and/or date associated with the healthcare claim transaction. In addition, a wide variety of information may be stored as desired in various embodiments of the invention, for example, a copy of the healthcare claim transaction, information extracted from the healthcare claim transaction, information associated with the processing of the generic notification module 180, information associated with generated or triggered rejections, etc. As desired in certain embodiments, billing information may be communicated to a suitable billing system associated with the service provider. In other embodiments, billing information may be stored for subsequent access by a billing system or for subsequent access by another component of the service provider for communication to the billing system. Billing information may be utilized by the billing system in order to charge customers of the service provider for the generic notification service provided by the generic notification module 180. A wide variety of different types of billing information may be stored and/or communicated as desired in various embodiments of the invention, for example, an identifier associated with the invocation of the generic notification module 180 or a billing code (e.g., a unique billing code) associated with the invocation of the generic notification module 180. As an alternative to storing or communicating billing information, the generic notification module 180 may set a billing code for the healthcare claim transaction to a unique billing code associated with the provided generic notification service. The unique billing code may be identified or recognized during subsequent processing of the healthcare claim transaction by either the billing system or a component of the service provider computer 106. The identified billing code may then be utilized by the billing system in the generation of bills for customers of the service provider.

In accordance with certain embodiments of the invention, one or more reports may be generated utilizing at least a portion of the stored information associated with the healthcare claim transaction. Reports may be generated by the generic notification module 180, the service provider computer 106, and/or a separate reporting module. A wide variety of different information may be included in a generated report, including but not limited to, information extracted from one or more healthcare claim transactions, information associated with rejections triggered by the generic notification module 180, invocation information associated with the generic notification module 180, invocation rate information for the generic notification module 180, financial information, billing information, etc. Additionally, generated reports may be formatted and/or sorted utilizing a wide variety of different parameters and/or criteria, such as identifiers for healthcare provider computers, identifiers for healthcare providers, identifiers of drugs and/or products associated with healthcare claim transactions, dates of service, etc. As desired, generated reports may be communicated to one or more recipients, such as the healthcare provider computer 104 and/or a healthcare provider back office computer.

It is appreciated that upon the healthcare provider computer receiving the reject message 320, the pharmacist or pharmacy assistant may counsel the patient regarding the upcoming availability of a generic equivalent. Thus, the patient may decide to delay filling or refilling a product until the generic equivalent is available. Alternatively, the patient may decide to fill or refill a lesser amount (e.g., 30 days supply instead of 90 days supply) of a branded or non-generic drug or product. Yet still, the patient may disregard the generic notification message, and decide to continue with the original fill or refill of the same quantity of the branded/non-generic drug or product. In any of these scenarios, the pharmacy healthcare provider computer 104 may generate another healthcare claim transaction request 325 for the requested product for the patient. The healthcare claim transaction request 325 may be communicated to the service provider computer 106. The service provider computer 106 may determine that the generic notification edit is enabled (block 407), and thus, provide a copy of the healthcare claim transaction request 325, a copy of the transaction request 325, and/or information included in the transaction request 325 may be communicated to the generic notification module 180 for processing. However, in this situation, one of blocks 410 (a generic product is identified) or 425 (a generic product is not identified, but a prior rejection has been recorded) will be satisfied, and the generic notification module 180 may mark the healthcare claim transaction request 325 as an approved or acceptable transaction to facilitate routing or communication of the healthcare claim transaction request 325 to the claims processor computer 108 by the service provider computer 106. As desired, the generic notification module 180 may communicate a message 330 indicating that the healthcare claim transaction request 325 is not affected by the generic notification edit, and the service provider computer 106 may route the healthcare claim transaction request 325 and/or perform additional processing on the healthcare claim transaction 325 based upon the receipt of the message 315. Upon adjudication of the healthcare claim transaction 325 by the claims processor computer 108, an adjudicated reply 335 may be provided to the service provider computer 106. The adjudicated reply 335 can indicate whether the claim request was paid or rejected, and if paid, the covered amount and/or the patient responsibility amount. The service provider computer 106 may optionally perform any post-edits prior to communicating the adjudicated reply in a response 335 to the healthcare provider computer.

Figure 3B:
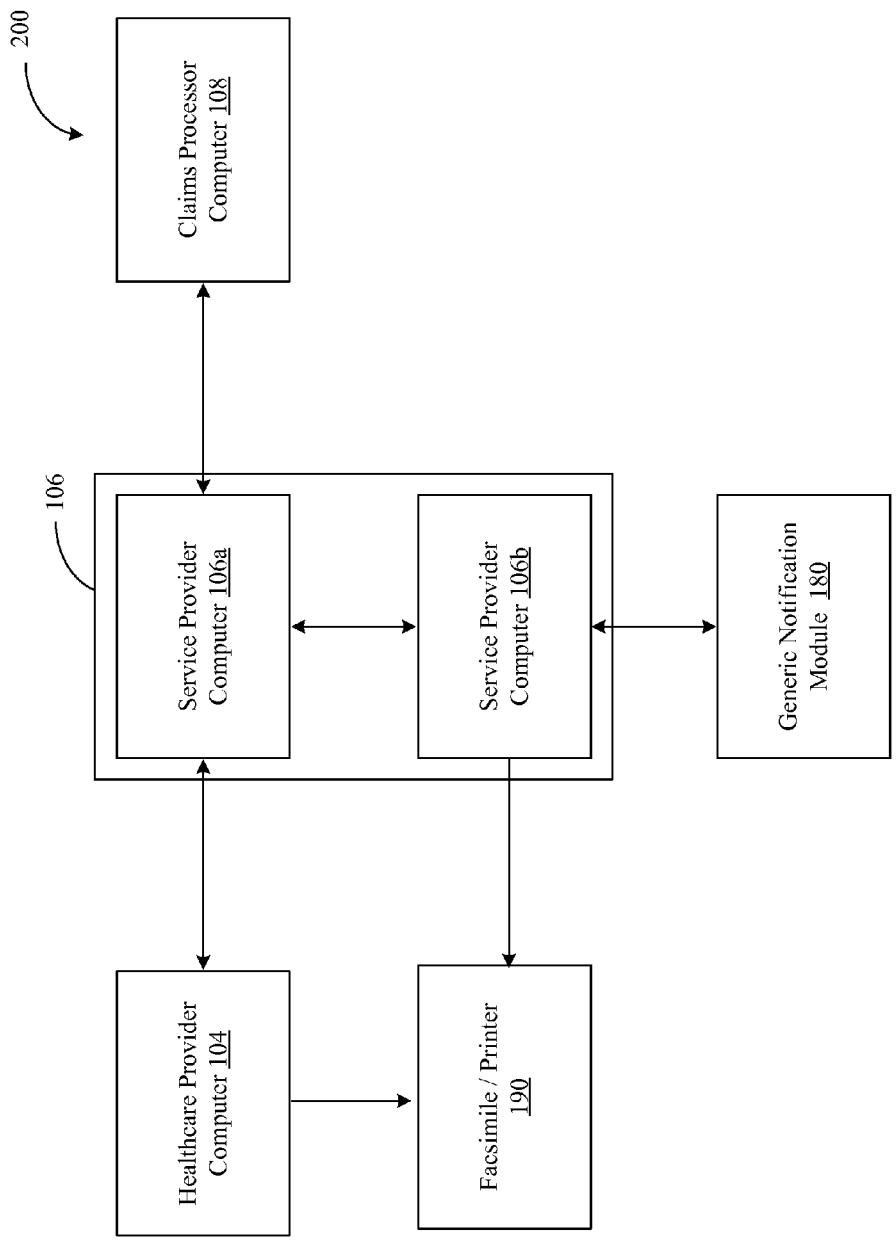

It will be appreciated that variations of the data flow 300 illustrated in FIG. 3A may be utilized in accordance with various embodiments of the invention. For example, as shown in FIG. 3B, the service provider computer 106 may be comprised of two or more distinct service provider computers 106a and 106b that are in communication with each other. Service provider computer 106a may be operative with one or more healthcare provider computers and claims processor computers, such as the healthcare provider computer 104 and claims processor computer 108 illustrated in FIG. 1. However, service provider computer 106b may have a data processing arrangement with service provider computer 106a. Under the data processing agreement, the service provider computer 106a may be permitted to utilize or offer services of the service provider computer 106b, including those of the generic notification module 180. For example, a first service provider may communicate claims and/or other information to a second service provider for processing. Likewise, the service provider computer 104b can be configured to deliver a printing or facsimile request to the facsimile/printer device 190.

Various block and/or flow diagrams of systems, methods, apparatuses, and/or computer program products according to example embodiments of the invention are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer readable program code or program instructions embodied therein, said computer readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method, comprising:
   receiving, from a healthcare provider computer, a healthcare claim transaction request that identifies a product for a patient;
   determining that the product identified by the healthcare claim transaction request is a non-generic product or a branded product;
   determining that a generic equivalent for the product identified by the healthcare claim transaction request will become available on a future date by accessing a database comprising one or more future dates of an availability of one or more generic equivalents to the non-generic drug or the branded product;
   generating a generic notification message indicating the availability of the generic equivalent for the product on the future date;
   delivering or directing a delivery of the generic notification message,
   wherein the above operations are performed by one or more computers associated with a service provider.

2. The computer-implemented method of claim 1, further comprising:
   prior to generating the generic notification message, further determining that the future date is within a predetermined time period from a current date associated with the healthcare claim transaction request,
   wherein the above operation is performed by one or more computers associated with a service provider.

3. The computer-implemented method of claim 1, wherein the generic notification message further specifies an expected price or savings associated with the generic equivalent.

4. The computer-implemented method of claim 1, wherein the healthcare provider computer is associated with one or more particular pharmacy locations, wherein the future date is based upon an expected delivery date of the generic equivalent to the one or more particular pharmacy locations.

5. The computer-implemented method of claim 1, wherein the generic notification message is delivered to the healthcare provider computer.

6. The computer-implemented method of claim 5, further comprising:
transmitting a reject response to the healthcare provider computer in response to the received healthcare claim transaction request, the reject response including the generic notification message,
wherein the above operation is performed by one or more computers associated with a service provider.

7. The computer-implemented method of claim 6, wherein the healthcare claim transaction request is a first healthcare claim transaction request, and further comprising:
storing information indicating a prior rejection of the healthcare claim transaction request identifying the product for the patient;
receiving, from the healthcare provider computer, a second healthcare claim transaction request that identifies the product for the patient, the product being a same product as for the first healthcare claim transaction request;
identifying a presence of the stored information indicating the prior rejection associated with the product for the patient; and
delivering the second healthcare claim transaction request to a claims processor computer for adjudication,
wherein the above operations are performed by one or more computers associated with a service provider.

8. The computer-implemented method of claim 1, wherein the generic notification message is delivered by at least one of: (i) via email, (ii) to a facsimile, (iii) to a printer, (iv) via text message to a cellular phone or personal communications device, (v) via Internet message or presentation, or (v) via paper mailing.

9. The computer-implemented method of claim 1, wherein the generic notification message is delivered to at least one of (i) a pharmacy; (ii) a healthcare provider; or (iii) the patient.

10. The computer-implemented method of claim 1, wherein the product is identified in the healthcare claim transaction request by a National Drug Code (NDC), a Universal Product Code, or a SKU number, wherein the product identified by the healthcare claim transaction request is determined to be a non-generic product or a branded product based upon the NDC, UPC, or SKU number.

11. A system, comprising:
at least one memory operable to store computer-executable instructions; and
at least one processor configured to access the at least one memory and execute the computer-executable instructions to:
receive, from a healthcare provider computer, a healthcare claim transaction request that identifies a product for a patient,
determine that the product identified by the healthcare claim transaction request is a non-generic product or a branded product,
determine that a generic equivalent for the product identified by the healthcare claim transaction request will become available on a future date by accessing a database comprising one or more future dates of an availability of one or more generic equivalents to the non-generic drug or the branded product,
generate a generic notification message indicating the availability of the generic equivalent for the product on the future date, and
deliver or direct a delivery of the generic notification message.

12. The system of claim 11, wherein the at least one processor is further configured to execute the computer-executable instructions to:
prior to generating the generic notification message, further determine that the future date is within a predetermined time period from a current date associated with the healthcare claim transaction request.

13. The system of claim 11, wherein the generic notification message further specifies an expected price or savings associated with the generic equivalent.

14. The system of claim 11, wherein the healthcare provider computer is associated with one or more particular pharmacy locations, wherein the future date is based upon an expected delivery date of the generic equivalent to the one or more particular pharmacy locations.

15. The system of claim 11, wherein the generic notification message is delivered to the healthcare provider computer.

16. The system of claim 15, wherein the at least one processor is further configured to execute the computer-executable instructions to:
transmit a reject response to the healthcare provider computer in response to the received healthcare claim transaction request, the reject response including the generic notification message.

17. The system of claim 16, wherein the healthcare claim transaction request is a first healthcare claim transaction request, and wherein the at least one processor is further configured to execute the computer-executable instructions to:
store information indicating a prior rejection of the healthcare claim transaction request identifying the product for the patient;
receive, from the healthcare provider computer, a second healthcare claim transaction request that identifies the product for the patient, the product being a same product as for the first healthcare claim transaction request;
identify a presence of the stored information indicating the prior rejection associated with the product for the patient; and
deliver the second healthcare claim transaction request to a claims processor computer for adjudication.

18. The system of claim 11, wherein the generic notification message is delivered by at least one of: (i) via email, (ii) to a facsimile, (iii) to a printer, (iv) via text message to a cellular phone or personal communications device, (v) via Internet message or presentation, or (v) via paper mailing.

19. The system of claim 11, wherein the generic notification message is delivered to at least one of (i) a pharmacy; (ii) a healthcare provider; or (iii) the patient.

20. The system of claim 11, wherein the product is identified in the healthcare claim transaction request by a National Drug Code (NDC), a Universal Product Code, or a SKU number, wherein the product identified by the healthcare claim transaction request is determined to be a non-generic product or a branded product based upon the NDC, UPC, or SKU number.

* * * * *